(12) United States Patent
Feiner et al.

(10) Patent No.: US 11,666,385 B2
(45) Date of Patent: Jun. 6, 2023

(54) SYSTEMS AND METHODS FOR AUGMENTED REALITY GUIDANCE

(71) Applicant: THE TRUSTEES OF COLUMBIA UNIVERSITY IN THE CITY OF NEW YORK, New York, NY (US)

(72) Inventors: Steven Feiner, New York, NY (US); Gabrielle Loeb, Wynnewood, PA (US); Alon Grinshpoon, New York, NY (US); Shirin Sadri, San Clemente, CA (US); Carmine Elvezio, Bellmore, NY (US)

(73) Assignee: The Trustees of Columbia University in the City of New York

( * ) Notice: Subject to any disclaimer, the term of this patent is extended or adjusted under 35 U.S.C. 154(b) by 449 days.

(21) Appl. No.: 16/796,645

(22) Filed: Feb. 20, 2020

(65) Prior Publication Data

US 2020/0188028 A1 Jun. 18, 2020

Related U.S. Application Data

(63) Continuation of application No. PCT/US2018/047326, filed on Aug. 21, 2018.

(60) Provisional application No. 62/643,928, filed on Mar. 16, 2018, provisional application No. 62/548,235, filed on Aug. 21, 2017.

(51) Int. Cl.
*A61B 34/10* (2016.01)
*G06N 20/00* (2019.01)
*G06F 3/16* (2006.01)
*G06T 19/00* (2011.01)

(52) U.S. Cl.
CPC ............ *A61B 34/10* (2016.02); *G06F 3/167* (2013.01); *G06N 20/00* (2019.01); *G06T 19/006* (2013.01); *A61B 2034/107* (2016.02); *A61B 2034/108* (2016.02)

(58) Field of Classification Search
CPC .......... A61B 34/10; G06T 19/00; G06F 3/16; G06N 20/00
See application file for complete search history.

(56) References Cited

U.S. PATENT DOCUMENTS 11,232,580 B2 * 1/2022 Tran .................... G06V 10/143
11,253,321 B2 * 2/2022 Amanatullah .......... G06T 19/20
(Continued)

FOREIGN PATENT DOCUMENTS

WO WO 2003/088143 A2 10/2003

OTHER PUBLICATIONS

International Search Report dated Nov. 5, 2018 in International Application No. PCT/US2018/047326.
(Continued)

*Primary Examiner* — Anil K Bhargava
(74) *Attorney, Agent, or Firm* — Baker Botts LLP

(57) ABSTRACT

Certain embodiments include a method for assisting a clinician in performing a medical procedure on a patient using augmented reality guidance. The method can include obtaining a three-dimensional model of an anatomic part of the patient. The method can also include aligning the three-dimensional model with data to form augmented reality guidance for the medical procedure. In addition, the method can include presenting the augmented reality guidance to the clinician during the medical procedure using an augmented reality three-dimensional display.

21 Claims, 9 Drawing Sheets

(56) References Cited

U.S. PATENT DOCUMENTS

| | | | |
|---|---|---|---|
| 11,350,072 B1* | 5/2022 | Quiles Casas | G06T 19/006 |
| 2005/0203380 A1* | 9/2005 | Sauer | G02B 7/002 |
| | | | 600/417 |
| 2016/0026253 A1* | 1/2016 | Bradski | H04N 13/128 |
| | | | 345/8 |
| 2016/0191887 A1* | 6/2016 | Casas | H04N 13/111 |
| | | | 348/47 |
| 2018/0049622 A1* | 2/2018 | Ryan | A61B 34/10 |
| 2021/0121237 A1* | 4/2021 | Fanson | A61B 34/20 |
| 2022/0168051 A1* | 6/2022 | Ryan | G02B 27/0093 |

OTHER PUBLICATIONS

Mitrovic et al., "Simultaneous 3D-2D image registration and C-arm calibration: Application to endovascular image-guided interventions," Med. Phys. 42 (11), 6433-6447, Nov. 2015.

* cited by examiner

SYSTEMS AND METHODS FOR AUGMENTED REALITY GUIDANCE

CROSS REFERENCE TO RELATED APPLICATION

This application is a continuation application of International Patent Application No. PCT/US2018/047326, entitled "SYSTEMS AND METHODS FOR AUGMENTED REALITY GUIDANCE," filed on Aug. 21, 2018, which claims priority to U.S. Provisional Patent Applications Nos. 62/548,235, entitled "STEREOSCOPIC OPTICAL SEE-THROUGH AUGMENTED REALITY GUIDANCE SYSTEM FOR VASCULAR INTERVENTIONS," which was filed on Aug. 21, 2017, and 62/643,928, entitled "HANDS-FREE INTERACTION FOR AUGMENTED REALITY IN VASCULAR INTERVENTIONS," which was filed on Mar. 16, 2018, the entire contents of which are incorporated by reference herein.

STATEMENT REGARDING FEDERALLY SPONSORED RESEARCH

This invention was made with government support under HL07616 awarded by the National Institutes of Health and 1514429 awarded by the National Science Foundation. The government has certain rights in the invention.

BACKGROUND

Augmented Reality (AR) has an increasing role in a variety of different industries. AR provides for an interactive experience of a real-world environment in which the objects that reside in the real-world are augmented by computer-generated information. For example, AR can be used in the entertainment space to enhance video gaming and social media applications. AR can also be used in different professional fields, such as archaeology, architecture, education, industrial or mechanical design, aerospace, tourism, retail, and/or marketing.

AR can also be used in connection with certain medical procedures. In particular, AR can be used along with certain patient imaging techniques to improve the performance of various medical procedures by creating a virtual environment in which three-dimensional virtual content can be integrated into the real world. Rather than being entirely immersed in a virtual world of the patient's anatomy, AR can superimpose virtual models on real patients and allow a clinician performing a procedure to see the patient and the patient's surrounding environment.

Vascular interventions are a type of medical procedure performed by a clinician in which a patient's blood vessels are used as a medium of transportation to reach the required area within the patient's body. Using vascular interventions, clinicians can embolize tumors, stop bleeds, treat aneurysms, reverse strokes, and even replace heart valves without the need for an invasive open surgical procedure. Due to the two-dimensional nature of certain imaging techniques, such as fluoroscopy, clinicians can have difficulty identifying vessels and determining their orientation. Navigating to the appropriate vessel using two-dimensional imaging can take an excessive amount of time, while increasing the patient's exposure to both contrast and radiation. In certain cases, clinicians resort to a cone-beam computed tomography (CT) scan to better visualize the vessels. Doing so, however, risks exposing the patient to additional radiation and contrast.

SUMMARY

The disclosed subject matter provides augmented reality guidance for performing medical procedures.

An example method can be used for assisting a clinician in performing a medical procedure on a patient using augmented reality guidance. The method can include obtaining a three-dimensional model of an anatomic part of the patient and aligning the three-dimensional model with live data to form augmented reality guidance for the medical procedure. In addition, the method can include presenting the augmented reality guidance to the clinician during the medical procedure using an augmented reality 3D display for the medical procedure.

Example apparatus can be used for assisting a clinician in performing a medical procedure on a patient using augmented reality guidance. The apparatus can include an augmented reality 3D display. The apparatus can also include at least one memory containing a computer program code. The apparatus also includes at least one processor for obtaining a three-dimensional model of an anatomic part of the patient, and aligning the three-dimensional model with live data to form augmented reality guidance for the medical procedure. In addition, the apparatus can present the augmented reality guidance to the clinician during the medical procedure using an augmented reality 3D display.

In certain embodiments, the memory and the computer program code are configured to cause the apparatus at least to obtain a three-dimensional model of an anatomic part of a patient. The memory and the computer program code can also be configured, to cause the apparatus at least to align the three-dimensional model with data to form augmented reality guidance for the medical procedure. In addition, the memory and the computer program code can be configured to cause the apparatus at least to present the augmented reality guidance to the clinician during the medical procedure using an augmented reality 3D display.

According to certain embodiments a non-transitory computer-readable medium encodes instructions that, when executed in hardware, perform a process. The process can include obtaining a three-dimensional model of an anatomic part of a patient and aligning the three-dimensional model with data to form augmented reality guidance for the medical procedure. In addition, the process can include presenting the augmented reality guidance to the clinician during the medical procedure using an augmented reality 3D display.

An apparatus, in certain embodiments, can include a computer program product encoding instructions for performing a process according to a method. The method includes obtaining a three-dimensional model of an anatomic part of a patient and aligning the three-dimensional model with data to form augmented reality guidance for the medical procedure. In addition, the method can include presenting the augmented reality guidance to the clinician during the medical procedure using an augmented reality 3D display.

DETAILED DESCRIPTION

Figure 1:
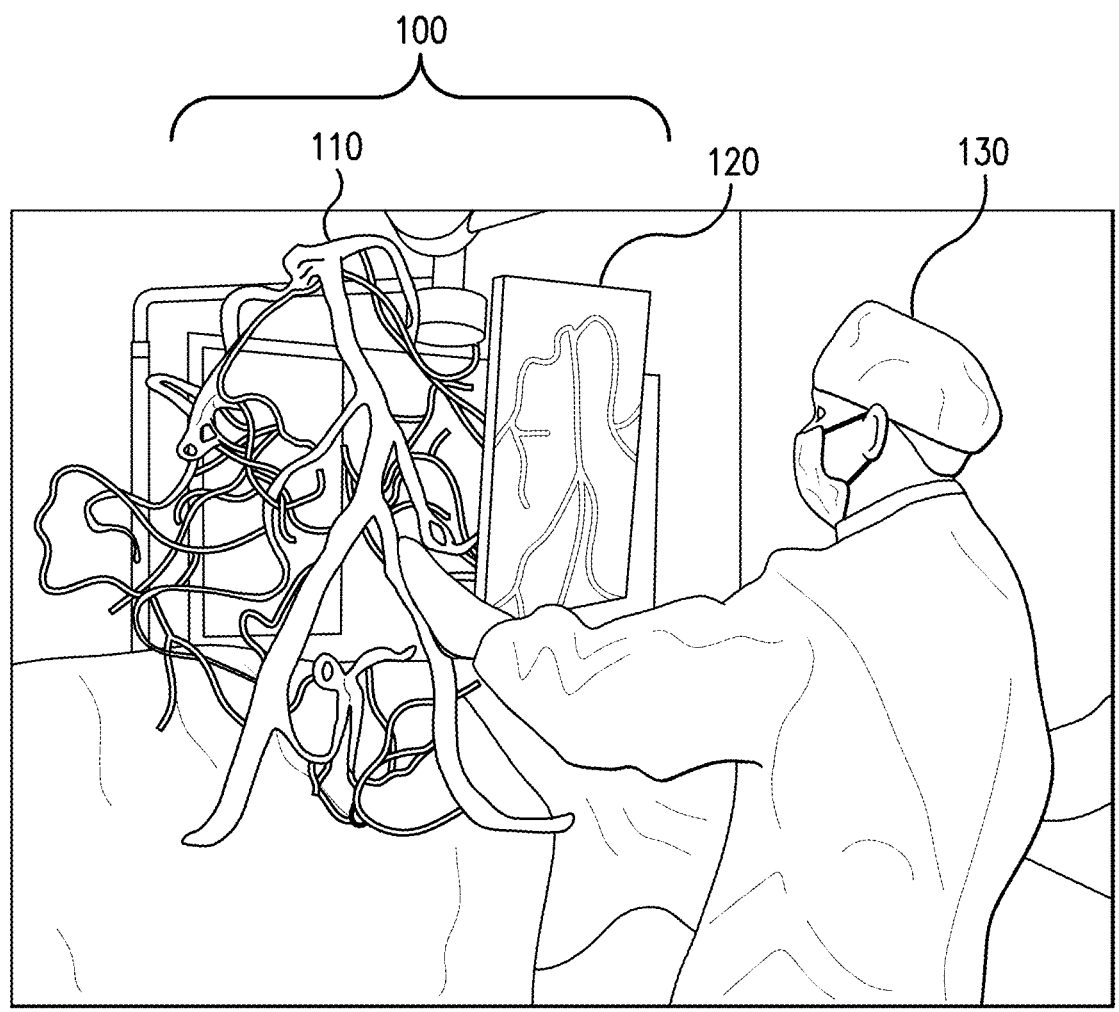
FIG. 1 is a diagram illustrating an exemplary AR guidance system according to some embodiments of the disclosed subject matter.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

In certain embodiments, AR guidance can be used to present perceptual information to a user (such as a clinician) to improve interaction by the user with the real-world environment when performing tasks in a variety of fields. The AR guidance described herein is suitable for use in a wide variety of applications, such as marketing, advertising, education, gaming, entertainment, industrial design, medicine, military and navigation. In accordance with an exemplary embodiment, the disclosed AR guidance is suitable and beneficial for use in medical applications, including for use by a clinician performing a medical procedure. For purpose of illustration of the disclosed subject matter only, and not limitation, reference will be made herein to AR guidance intended for use by a clinician performing vascular surgery.

In one example, AR guidance can be used to present information useful to a clinician while performing a medical procedure, including information useful to the procedure obtained using a first modality, either before or during the procedure, in alignment with information measured or acquired during the procedure using a second modality. Use of AR guidance can help to improve the performance of a medical procedure by the clinician, for example, by reducing procedure times, radiation exposure, contrast dose, and complication rates. Using AR guidance can also help to facilitate access to difficult areas of the patient's body, and eliminate guesswork involved in locating certain vessels.

AR can be used to improve performance of a variety of medical procedures. In one non-limiting example, the AR guidance described herein can be used in the performance of a digital neuro or cerebral angiogram. By providing imaging of a vascular system, AR guidance can be used to improve vascular interventions, such as interventional radiology. In certain other embodiments, AR guidance can be used to facilitate cardiovascular surgery, such as transcatheter aortic valve replacement (TAVR) or mitral valve replacement (MVR). For example, AR guidance can be used by a doctor during placement and/or removal of filters in the patient's vascular system to collect debris during TAVR or MVR procedures.

In yet another embodiment, AR guidance can be used for an abdominal aortic aneurysm (AAA) repair to treat an aneurysm. In one example, AR guidance can be used for AAA open repair, which requires an incision in the abdomen to expose the aorta, while in another example, AR guidance can be used for endovascular aneurysm repair (EVAR) to place a stent and graft to support the aneurysm. The above medical procedures are merely exemplary procedures that can benefit from AR guidance. AR guidance can also be used for any other medical procedure, including non-vascular procedures and/or other fluoroscopy-guided procedures, such as organ transplantation, CT-guided biopsies, neurosurgical procedures, or spinal procedures.

In one non-limiting example, AR guidance can be used for vascular interventions. Using AR can make medical procedures involving vascular interventions faster, safer, and more cost-effective, while improving clinical outcomes for patients. For purpose of illustration, and not limitation, an auto-transforming three-dimensional virtual model of the patient's vessels, for example, can improve speed, accuracy and precision in identifying or locating a certain vessel, while helping to facilitate access to difficult vessels. In some embodiments, the AR guidance system can reduce radiation and contrast exposure associated with medical imaging techniques.

Figure 2:
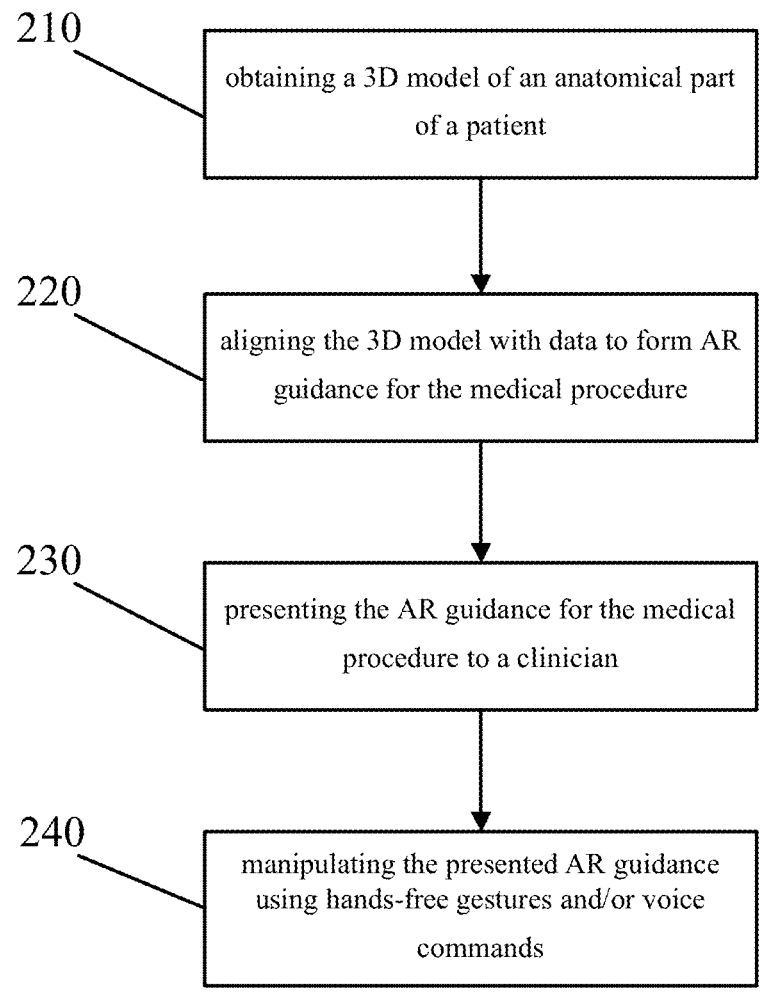
FIG. 2 is a flow chart illustrating exemplary AR guidance techniques according to some embodiments of the disclosed subject matter.

For purpose of illustration, and not limitation, reference is made to the exemplary embodiment of an AR guidance system 100 shown in FIG. 1. Additionally, for purpose of understanding, reference is made in conjunction to the method 200 of FIG. 2, which illustrates techniques for implementing and using AR guidance 100. For purpose of illustration and not limitation, and as embodied herein, FIG. 1 shows exemplary AR guidance 100 presented to a clinician 130 during a procedure. The AR guidance 100 includes both a 3D model 110 and live data 120. At 210, the 3D model 110 can be obtained, for example and without limitation, either before or during the procedure, as discussed further herein. The 3D model can be a model of an anatomical part of a patient. At 220, the 3D model can be aligned with data 120 to form the AR guidance 100 for the procedure, as discussed further herein. For purpose of illustration, and not limitation, data 120 can include live imaging data, such as live 2D fluoroscopy of the patient's anatomy taken during the procedure. Additionally or alternatively, data 120 can include data related to the procedure obtained prior to the procedure.

At 230, the AR guidance 100 can be presented to the clinician 130 during the procedure, as discussed further herein. For purpose of illustration and not limitation, and as embodied herein, the AR guidance 100 can be presented to the clinician, at least in part using a 3D display. At 240, the AR guidance 100 can be manipulated by the clinician 130. For purpose of illustration and not limitation, as embodied herein, the AR guidance 100 can be manipulated by the clinician 130 using hands-free gestures or voice commands, or a combination thereof, which can allow for the clinician 130 to manipulate the AR guidance 100 while the clinician's 130 hands are otherwise occupied with performing the procedure. Additionally or alternatively, the AR guidance 100 can be manipulated by the clinician using hand gestures. Exemplary manipulations can include, for example and without limitation, rotating, scaling, moving, annotating, or changing display properties (e.g., color, brightness, contrast, transparency) of the AR guidance 100, as discussed further herein.

Figure 3:
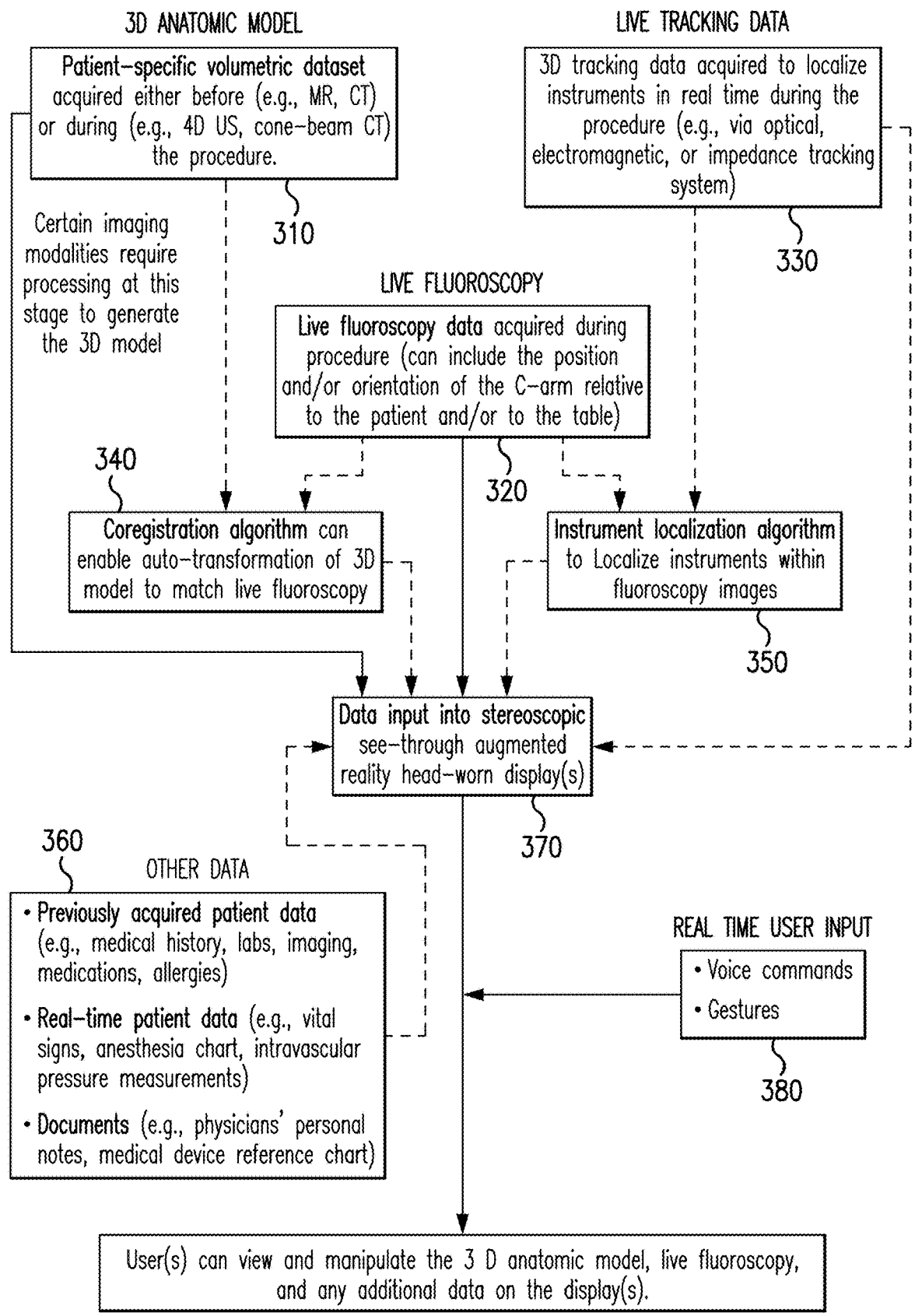
FIG. 3 is a diagram illustrating additional details of exemplary AR techniques according to some embodiments of the disclosed subject matter.

Referring now to FIG. 3, additional details of the AR guidance 100 and method 200 are provided. FIG. 3 describes a technique and system for AR guidance used by a clinician 130 during a medical procedure, such as a vascular intervention. As shown in FIG. 3, the AR guidance 100 can include a three-dimensional (3D) anatomic model 310. The 3D model 310 can be of a model of any portion of the patient's anatomy undergoing or relevant to the procedure, for example, the patient's vasculature, an organ, or any other part of the patient's anatomy. For purpose of illustration and not limitation, as embodied herein, the 3D model 310 can be obtained from a patient-specific volumetric dataset. For example, and not limitation, the 3D model 310 can be obtained from magnetic resonance imaging (MRI) a CT scan performed on the patient, or other forms of volumetric imaging, which results can be referred to as the patient-specific volumetric dataset. In other embodiments, the 3D model 310 can be created during a given procedure using, for example, a cone-beam CT or a four dimensional (4D) ultrasound model. In yet another embodiment, the 3D model 310 can be created using any other available method known to a person of ordinary skill in the art.

In certain embodiments, the 3D model 310 of the patient's vasculature can be aligned or transformed with data 320, such as live data, to form the AR guidance 100 to be presented to the clinician 130 while performing a medical procedure. The aligning of the 3D model 310, for example, can include fusing the 3D model 310 with data 320 acquired related to the patient's anatomy or physiology being monitored during the medical procedure. For example, the data 320 can be live image data, which can be obtained using two-dimensional (2D) fluoroscopy, a CT scan, X-ray, ultrasound, or any other available method. Additionally or alternatively, data 320 can include data related to the procedure obtained prior to the procedure. Live 2D fluoroscopy data, for example, can be acquired during the performance of a medical procedure on a patient. In one non-limiting example, the live 2D fluoroscopy data can be generated using a C-arm, which can refer to a mobile medical imaging device that is based on X-ray technology. The C-arm can be used to allow for the capturing of live 2D imaging during a medical procedure.

The AR guidance 100 can utilize the 3D model 310 and the data 320 as part of the medical procedure. As shown in 340 of FIG. 3, in one example, 3D model 310 and live 2D fluoroscopy (or other data 320) can be fused together to align the 3D model 310 with the data 320 to form the AR guidance 100. In one example, 3D model 310 and live 2D fluoroscopy can be fused using a co-registration algorithm, which can allow for transformation of the 3D model 310 to match the live fluoroscopy. The fused 3D model 310 and the live 2D fluoroscopy can then can be presented together in alignment on a 3D AR display. Alternatively, the 3D model 310 can be aligned with live 2D fluoroscopy presented on an external monitor. For example, the 3D model 310 can be aligned, using markers, trackers, or any other method known in the art, and presented using the 3D display in alignment with an external monitor presenting the 2D live data. In certain embodiments, machine learning tools, such as a convolutional neural network (CNN), can be used to align the 3D model 310 and the data 320.

Various techniques can be used to obtain orientation and/or position information for the C-arm for use in aligning the 3D model with the live data. For example, the C-arm can include software that outputs orientation and/or position coordinate information for use in forming the AR guidance 100. Alternatively, for example if no orientation and/or position coordinate information is available, other techniques can be used to track movement of the C-arm for use to align the 3D model with the live data. For example, an inertial measurement unit (IMU) can be installed on the C-arm to output orientation information for the C-arm. Additionally or alternatively, the orientation and/or position of the C-arm can be tracked using a camera in a smartphone, which can receive a signal from the IMU or can track a fiducial marker, such as a printed paper marker or other suitable marker, attached to the C-arm, to determine the relative movement of the C-arm.

In addition, or as a further alternative, optical character recognition (OCR) can be used to obtain the orientation and/or position information for the C-arm. For example, the C-arm software can output orientation and/or position coordinate information onto a 2D display. The coordinate information of the C-arm can then be read from the 2D display by the AR guidance system. The orientation and/or position of the C-arm can then be used by the AR guidance system to align the 3D model with the live data. As further alternatives, any other suitable method can be used to track the position and orientation of the C-arm. For example, aligning can include at least one of machine learning, OCR, input from an inertial measurement unit, physical trackers, or image recognition.

Referring again to FIG. 3, the 3D model 310 and the data 320 can be aligned using machine learning techniques. In one non-limiting example, the alignment can be performed using co-registering, as shown in 340 of FIG. 3. For example, machine learning, such as CNN, can be used to predict an affine transformation matrix that, when applied to a 3D CT dataset, most closely matches the projection plane of a given fluoroscopy image. In this manner, the affine transformation matrix can be used to predict co-registering of the 3D model and the live 2D fluoroscopy. The input to the CNN can be any live data images, such as a 2D fluoroscopy, CTs, X-rays, or digitally reconstructed radiographs generated from CTs. Using these images as training data, the CNN can learn to predict the affine transformation matrix that accurately co-registers each digitally reconstructed radiograph or fluoroscopy image with the 3D CT dataset. To implement the affine transformation matrix, a computer vision algorithm can be used to perform image processing of the live fluoroscopy to co-register it with a 3D model.

As shown in 330 of FIG. 3, certain embodiments can include using live tracking data, for example for instrument localization performed in real time. Live tracking data can be 3D tracking data acquired to localize instruments in real time during the procedure. For example, live tracking data can be acquired via optical, electromagnetic, or impedance tracking systems. Live tracking data can be used along with live fluoroscopy to localize instruments within the fluoroscopy image, as shown in 350.

Instrument localization, in some embodiments, can be performed by using the live tracking data, shown in 330, or using computer vision. For example, as shown in 350, an instrument localization algorithm can use computer vision or electromagnetic tracking to localize instruments within the AR guidance 100. Additional or alternative techniques can be used for localization. For example, computer vision can be used to localize intravascular instruments on the 3D model, either by triangulating its depth when using dual plane fluoroscopy or by assuming that it can coincide with the 3D model when using single plane fluoroscopy.

For purpose of illustration and not limitation, as embodied herein, catheter or wire localization and/or tracking can be used. For example, as a catheter is being inserted into a patient, the position, location, and/or orientation of the catheter can be detected or tracked. The tracking of the catheter can be presented within the 3D model or AR guidance using 3D tracking. The tracking can also be performed at part of the live 2D fluoroscopy display. Any known method can be used to track the catheter, such as 3D tracking or 2D display marking.

The data produced or obtained in any or all of 310, 330, 340, and 350 of FIG. 3 can be input into the AR guidance 100, which can display the AR guidance for the medical operation on an AR display or system. For purpose of illustration and not limitation, as embodied herein, the AR guidance can be presented using an augmented reality 3D display, which can be a head-worn display. The AR guidance display can include an IMU or a six-degree-of-freedom tracking technology (e.g., 3D position and 3D orientation) to provide additional inputs to the AR guidance system. In one specific embodiment, the AR guidance display can have networking capabilities. For example, the display can communicate using a local area network (LAN) and/or wirelessly with a clinician's medical equipment. Wireless communication can utilize, for example, wireless local area network (WLAN), Long Term Evolution (LTE), LTE Advanced (LTE-A), fifth generation (5G), or Internet of Things (IoT) technology. The clinician's medical equipment can include a smartphone, laptop, or any other electronic device used by the clinician.

The AR display, for example, can be an optical see-through display that allows users to see the real world directly through a transparent display or a video see-through display that allows users to see the real world imaged through one or more cameras. In one example, the display 370 can be a stereoscopic optical see-through head-worn display or video see-through head-worn display. In non-limiting embodiments, the optical see-through display can include a commercial display (e.g., Microsoft HoloLens). Head-worn display 370 can provide a clinician with the current position of their instrument within the 3D model, allowing them to navigate without the need for mental calculations or manual adjustment of the 3D model every time the C-arm, table, or patient moves. Alternatively, the AR guidance 100 can be displayed using a table-top 3D display, a full-room 3D display, or any other suitable display for presenting the 3D model 310 in alignment with data 320, which as discussed, can be displayed on the AR display or on an external monitor in alignment with the AR display.

The AR guidance can be configured to reduce radiation and/or contrast exposure to the patient during a medical procedure. In one example, the clinician 130 using the AR guidance 100 can gaze, rotate their head, or look away from the patient during the medical procedure. When the clinician looks away from the patient, imaging of the data 320 (along with the 3D model 310, if being obtained in real time) can be paused, thereby limiting the radiation and/or contrast associated with acquiring images of the patient's anatomy. In this manner, the amount of radiation and/or contrast a patient is exposed to during the medical procedure can be reduced.

In some embodiments, the 3D model 310 and/or the live 2D fluoroscopy (or other data 320) can appear as virtual objects presented by the 3D display. The clinician 130 can provide input in real time, as shown in 380 in FIG. 3, to manipulate the virtual 3D model or 2D fluoroscopy, while maintaining a sterile environment during the performance of the medical procedure. The real time user input, for example, can include hand gestures, or alternatively, can include hands-free input or interaction, such as head gestures, eye gazes, voice commands, or other input to manipulate the 3D display. Manipulations can include rotating, scaling, moving, annotating, or changing display properties (e.g., color, brightness, contrast, transparency), to either the 3D model 310 or, if displayed together using the 3D display, the data 320. Manipulations can also include updating or changing the type of data displayed, for example, to display another 3D model of a different anatomical area of the patient, show previously acquired 2D live data images or other data 320, or show information from patient medical records.

In certain embodiments, the clinician 130 can use zero-order control and/or first-order rate control to manipulate the AR guidance 100. Zero-order control can be used to control the position of an object, and first-order control can be used to control a rate of movement of an object. Rate control can map human input to the velocity of the object movement. For example, to perform either zero-order control or first-order rate control, the clinician uses hands-free gestures, such as head movement or rotation, changing eye gaze, verbal commands, hand gestures, manual input with a controller, and/or any combination thereof. Hands-free gestures can allow a clinician to perform a medical procedure while leaving the clinician's hands free to perform the medical procedure. Hands-free gestures can be used in combination with voice commands to manipulate the AR guidance 100. For example, the clinician can verbalize a command to select a particular manipulation to perform, and then can use hands-free gestures, such as head movement or eye movement, to perform the manipulation. In certain embodiments, therefore, the manipulation of the AR guidance can include using a head gesture to perform at least one of first-order control or zero-order control, where the first-order control comprises at least one of the rotating or scaling of the augmented reality guidance, and the zero-order control comprises the moving of the AR guidance.

Figure 4A:
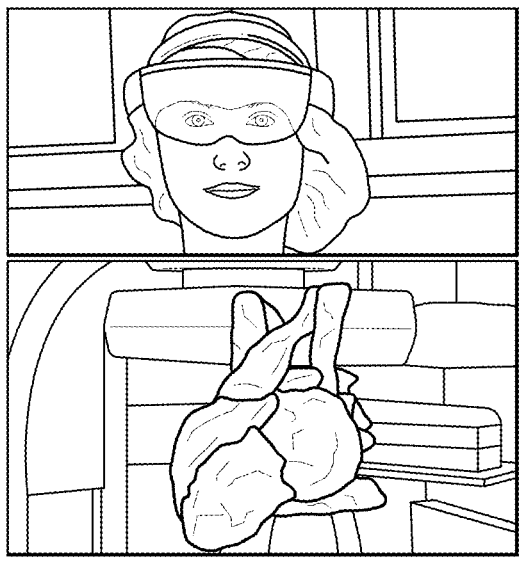
FIG. 4A-4C each is a schematic diagram illustrating additional details of exemplary AR techniques according to some embodiments of the disclosed subject matter.
Figure 4B:
Figure 4C:

FIG. 4A-4C are schematic diagrams illustrating additional details of exemplary AR techniques according to some embodiments of the disclosed subject matter. In particular, FIG. 4A-4C shows first-order mapping of a user's head orientation to model rotation speed of the 3D model, for purpose of illustration and not limitation. As shown in the example embodiment of FIG. 4A, a user can select a transformation mode by looking at the model. If a rotation mode is selected, the 3D model can rotate in the same direction as the head, in certain embodiments. As shown in FIG. 4B, a rotation of the user's head to the right can cause a rotation of the 3D model to the right. Using first-order rate control, as the user's head is oriented further away from the center of the 3D model, the transformation can be applied at a faster rate, as shown in the example of FIG. 4C. In some embodiments, small changes to the head orientation can adjust transformation or manipulation of the 3D model, as shown in FIGS. 4B and 4C.

Figure 5A:
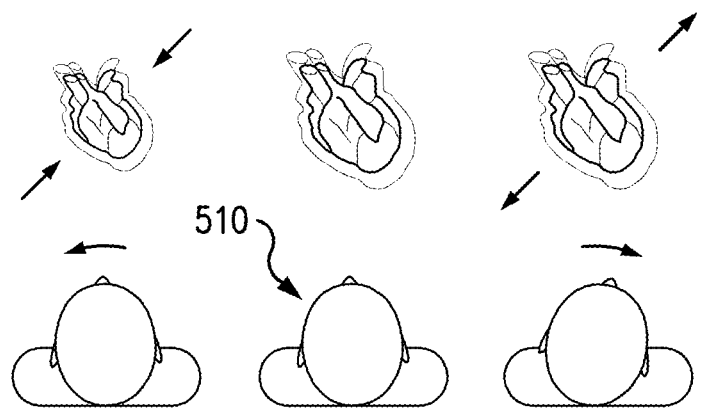
FIGS. 5A-5D each is a schematic diagram illustrating additional details of exemplary AR techniques according to some embodiments of the disclosed subject matter.
Figure 5B:
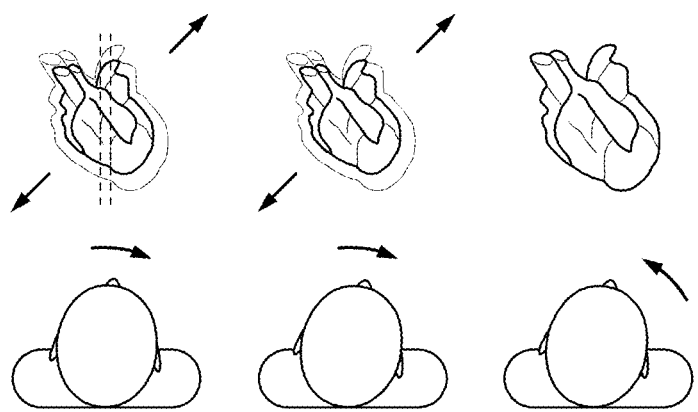

For purpose of illustration and not limitation, to scale the 3D model, the clinician can verbalize the command "scale," and then can rotate their head to adjust the scale of the 3D model to a degree or at a rate corresponding to the magnitude of the head movement, as shown for example in FIGS. 5A and 5B.

Referring now to FIGS. 5A-5D, exemplary techniques for manipulation of the AR guidance 100 using hands-free gestures are illustrated according to some embodiments of the disclosed subject matter. In particular, FIGS. 5A-5D illustrate that translation and rotation of the user's head can be used to transform a 3D model used in AR guidance for vascular intervention. The user's head pose can control the view of the AR guidance, while first-order control can be used for scaling and rotating the 3D. In certain embodiments, the further the head is rotated from the model center, the faster the transformation occurs. The transformation can be applied when the user is not looking toward the model's center window. The center window can be a predefined distance to the left and right of the model center.

FIGS. 5A and 5B illustrate an exemplary use of first-order control. In FIG. 5A, rotating a user's head 410 to the right can upscale or make the model larger, while rotating a user's head to the left can downscale or make the model smaller. FIG. 5B illustrates that the further away a user's head is oriented from facing the model center, the faster the transformation is applied. To cease the manipulation of the 3D model, the user can orient their head back toward the center of the model by a predetermined degree of movement. The predetermined degree of movement can be selected from a range, for example, from 0.1° degree to 10°. In another example, any other predetermined degree of movement can be used. As the clinician's real-world distance from the model increases, a smaller angle can be used to cause the system to initiate the transformation. For example, when the clinician is a yard away from the model, the angle recognized to cease the manipulation can be smaller than the angle required when the clinician is a foot away from the model. In certain embodiments, therefore, when the 3D model is located further away from the clinician, the model occupies less of the clinician's field of view, thereby allowing the clinician to rotate their head further without losing sight of the model. Alternatively, the angle recognized to cease manipulation can be constant, or otherwise independent of the distance of the clinician from the model.

In certain embodiments, tilting/moving a clinician's head back toward a center window more than a threshold amount can pause or cease the manipulation. In certain embodiments, the center window may be in the shape of a circle or other shape located at or around the center of the object. The center window in FIG. 5B is indicated by a pair of dotted lines. When the clinician's direction of gaze moves outside the center window, a clinician's head tilted back towards the center of the model beyond a predefined cursor window can pause the manipulation. A cursor, which provides visual cues for the users, can appear in front of the user and follow the user's forward-facing head vector. Rotating the clinician's head more than a threshold amount away from the cursor can be faster than rotating the head all the way back to center, and can allow a manipulation or transformation to be paused quicker. In addition, a clinician can exit a manipulation or transformation by verbalizing a command, such as "stop," "pause," "exit," or any other suitable term. In certain other embodiments, any eye movements, gaze tracking, or image-based facial motion or orientation can be used to cease the manipulation of the 3D model. In certain other embodiments, hand gestures or controller input can be used to cease the manipulation of the 3D model.

Figure 5C:
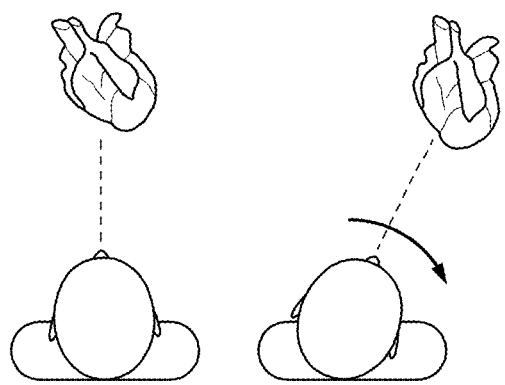

FIG. 5C illustrates using zero-order control to manipulate the AR guidance 100, for example by translating the 3D model. For example, in FIG. 5C a hands-free manipulation can cause the 3D model to translate and rotate with the movement of the head, as if the model were rigidly attached to head at an offset. Additionally or alternatively, in FIG. 5D, a clinician's head pose can be mapped to a model transformation. The clinician's head, for example, can be rotated slightly to the right and rolled slightly counterclockwise to perform a manipulation.

Figure 5D:
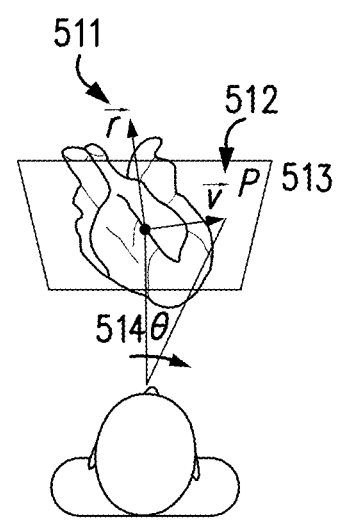

In certain embodiments, the transformation modes can be made available to a clinician via a hands-free manipulation. The manipulation, for example, can be rotating, scaling, moving, sizing, or changing the transparency and/or coloring of the AR guidance. In one non-limiting example, hands-free rotation can be activated by verbalizing the command "rotate" (or other suitable term) to enter a rotation mode. Rotation, in some embodiments, can be counterclockwise about axis $\vec{r}$ 511 passing through the model center in a plane P 513 perpendicular to the vector between the head and the model center, as shown in FIG. 5D. Vector $\vec{v}$ 512 between the model center and the intersection of the forward-facing vector of the head with P 513 determines the rotation rate. Axis $\vec{r}$ 511 can be obtained by rotating $\vec{v}$ 512 counterclockwise 90° in plane P 513.

In another example, a hands-free scaling mode can be activated by verbalizing the command "resize" or "scale" or another suitable term to enter a scaling mode. In one embodiment, scaling can be isotropic, ranging from twice to half the default size of the model. Vector $\vec{v}$ 512 projected onto the projection of the head x axis onto P 513 can determine the scaling magnitude. Rotating the head to the right or left of the up vector of the head will make the model grow or shrink, respectively. In an alternative embodiment, the model can be scaled up when the intersection of the forward-facing vector of the head with P 513 is above and to the right of the line u=−v, where u and v establish a Cartesian coordinate system in P 513, with the origin at the model center. The model can be scaled down when the intersection of the forward-facing vector of the head with P 513 is below and to the left of line u=−v.

In one example embodiment, the non-continuous, frame-dependent transfer function that defines the rate of control can be represented by the following equation:

$$CD(\vec{v}) = \begin{cases} 0, & 0 < \|\vec{v}\|, c_1 \\ \beta\|\vec{v}\|, & \|\vec{v}_{prev}\| \le \|\vec{v}\| \\ 0, & \|\vec{v}_{prev}\| - \|\vec{v}\| > c_2 \end{cases} \quad (1)$$

$$\|\vec{v}\| = |\tan \theta| \cdot D.$$

$\vec{v}_{prev}$ is set to the value of $\vec{v}$ from the previous frame only when $\vec{v}_{prev} < \vec{v}$, $\beta$ denotes the gain increase factor, $c_1$ and $c_2$ are the constant-gain thresholds of the center window and cursor window, $\theta$ is the angle between the vector from the head to the model center and the current forward-facing vector from the head to the model center and the current forward-facing vector of the head, and D is the distance from the head to the model.

In yet another example, a hands-free movement mode can be activated by verbalizing the command "move" (or other suitable command). In this mode, the model can remain rigidly locked to the clinician's head at its current offset and move along with the clinician's head position or eye gaze until the clinician verbalizes a termination command, such as "stop" or another suitable command.

Referring again to FIG. 3, the clinician can view and/or manipulate the 3D anatomic model, live fluoroscopy, and any other additional data on the display, as described herein. The 3D model can be manipulated to match live 2D fluoroscopy to compensate for patient movement, for example, from breathing or heartbeat, and movement of the C-arm. In some embodiments, the disclosed system can automatically adjust the 3D model to match the live fluoroscopy. The 2D fluoroscopy can be rendered in relation to the 3D model. For example, the 3D model can be aligned in front of the 2D fluoroscopy with the ability to adjust transparency such that it does not interfere with the clinician's ability to see the virtual fluoroscopy. The 2D fluoroscopy can be merged with the 3D model for binocular stereoscopic viewing.

The AR guidance, in some embodiments, can play back the fluoroscopy images in AR. This playback can allow clinicians to go back and reexamine data previously provided by the live fluoroscopy. In other words, one or more parts of the AR guidance can be stored in a memory, and retrieved at the clinician's request.

As discussed above, in one non-limiting example, the 2D fluoroscopy can be merged with a 3D model to provide for binocular stereoscopic viewing. In other embodiments, however, a monocular monoscopic view can be provided. In one example embodiment, the AR guidance can map the information from the 2D image into a second eye's view of the 3D model.

In some embodiments, the AR guidance can allow a clinician to use a cutting plane to peer inside the 3D model. For example, a clinician can see the vessels within a liver or look inside a chamber of the heart. The plane can be controlled by hands-free gestures, voice commands, hand gestures, controller input, or any combination of these.

In certain embodiments, the AR guidance can display either the same, similar, or different virtual object to multiple users each using one or more AR displays. The system, in other words, can provide guidance to multiple clinicians during medical procedures. This sharing can help to facilitate communication during the performance of a medical procedure that requires multiple medical professionals. In other embodiments, sharing the AR guidance with a plurality of users concurrently can help to facilitate a discussion regarding anatomy as part of training staff members, educating students, or helping patients make informed medical decisions.

The AR guidance system, in certain embodiments, can adjust the size of a 3D model to correspond to its actual size in the patient's body. This size adjustment can allow a clinician to plan for a medical procedure and select the appropriate medical device to use for performing the medical procedure. For example, a clinician can hold up an intravascular device inside the virtual model of the patient's vasculature to determine whether the device fits within the desired location, and can adjust their plan or the size of the intravascular device accordingly. In some embodiments, the 3D model can be streamed into the AR environment in real time, for example, through wireless communication, allowing the 3D model to be created and updated in real time.

In certain embodiments, the augmented reality system can monitor the clinician's head and/or eye movement. Based on the clinician's gaze, head movement, and/or eye movement, the augmented reality system can automatically turn off the radiation of the C-arm applied to the patient when the clinician is not looking at the real or virtual fluoroscopy displays. In other words, the system can control the radiation such that the focus point of the clinician's gaze on the patient's body receives the full radiation dose, whereas the areas at the periphery of the clinician's focus point on the patient's body receive less in a graded fashion. This can help to reduce the patient's radiation exposure without interfering with the clinician's ability to interpret the fluoroscopy.

As discussed herein, a user can manipulate the 3D model via a hands-free gesture and/or voice command, and the system can include a 3D user interface that can be used to adjust the model's size, position, orientation, or transparency while maintaining sterility. The user interface, in some embodiments, can provide instructions and/or train users to perform the handsfree gestures and invoke the various features of the system. This can help users to better familiarize themselves with the interaction techniques defined by the system and help guide the actions of the users in the augmented reality environment. The user interface can also provide for a simulation of the AR guidance, which can be used for training purposes. In certain other embodiments, hand gestures can be used along with handsfree gestures to manipulate the 3D model.

In certain embodiments, other data can be inputted and displayed as part of the AR guidance. For example, as shown in 360 of FIG. 3, previously acquired patient data, such as medical history, labs, imaging, medications, and/or allergies can be displayed. Real-time patient data, such as vital signs, anesthesia chart, or intravascular pressure measurements, and/or other documents, such as clinicians' personal notes or a medical device reference chart can also be inputted and displayed.

With continued reference to FIG. 3, the AR guidance can receive input data and visualize it on the display. Input data can include at least one of patient-specific volumetric data 310, live 3D tracking data 330, previously acquired/real-time patient data or documents 360, or real-time user inputs 380. The AR guidance system can also allow for 3D annotation, such as drawing or erasing, multi-user view, and auto-scaling to match true size in patient's body. The AR guidance system can also allow for radiation reduction using gaze tracking, eye tracking, or head movement to pause or turn off the 2D fluoroscopy when a user is not gazing at the fluoroscopy.

In some embodiments, the AR guidance can record data. The data recorded can include saving all or part of any data from the medical procedure such as the 3D model, fluoroscopy, tracking data, audio, or video. As discussed above, the AR guidance can use auto-transformation to align or match the 3D model and the live data, for example, using a co-registration algorithm 340, and/or localizing instruments on the 3D model itself via 3D tracking or an instrument localization algorithm 350.

The live data, such as 2D fluoroscopy, and 3D model can be aligned. The aligning can be performed by at least one of making either the 3D model or the fluoroscopy visible to only the user's dominant eye, while the other remains visible to both eyes, and/or by mapping the fluoroscopy directly onto the 3D model as seen by both eyes. Mapping the fluoroscopy directly onto the 3D model, as seen by both eyes, can be performed either by mapping the other eye for which the 3D model has not been aligned with the otherwise unmodified fluoroscopy, or by mapping to both eyes if the user does not need to view the fluoroscopy from the same viewpoint as it was acquired. In such an embodiment, 3D tracking or computer vision can be used to distinguish vessels that overlap on the AR guidance.

In certain embodiments, hands-free interaction techniques, such as voice or head tracking, can be used to interact with the 3D virtual content in the AR guidance system, while making both hands available intraoperatively. Manipulation of the AR guidance model that appears to reside in the surrounding environment can be performed through small head rotations using first-order control, and rigid body transformation of those models using zero-order control. This allows the clinician to manipulate the model while staying close to the center of the field of view, thereby not causing any interference with the procedure being undertaken by the clinician.

As discussed herein, a user interface can be used to manipulate the 3D model in the AR guidance system using voice or head tracking. To ensure that the user is aware of system status, a cursor can appear in front of the user along the forward-facing vector of the user's head. The user can select a virtual model by moving and rotating their head until the cursor collides with that model. The user can issue a voice command to select a mode, which can be indicated by the cursor icon.

In one example, the AR guidance can identify the user. Each user, such as a clinician, can have a user-based profile associated with the user. The profile can be kept in a centralized storage location, along with the profile of other users. When the user begins using the AR guidance system, the system can be capable of automatically detecting the user and loading the user profile into the system. In other embodiments, the user can have to login to the AR guidance system, at which point the AR guidance system can load a user-based profile. One or more settings of the AR guidance can be adjusted based on the user-based profile. The user-based profile can include user-specific preferences for AR guidance, such as positioning of virtual objects within a procedure room and/or type of data displayed.

The AR guidance, in certain embodiments, can provide the user feedback during the performance of the medical procedure. The feedback can be based on the 3D model or the live data utilized by the AR guidance. The feedback, for example, can be audio, visual, haptic, or any other feedback. In one example, if a clinician inserts a catheter into the wrong vessel, a visual alert can be shown on the 3D model.

In some embodiments, the user can annotate the AR guidance in an annotation mode. The user can enter the annotation mode using a voice command, a hand gesture, a head gesture, controller, and/or eye gazing. Once in the annotation mode, the clinician can annotate the AR guidance, such as highlighting, adding text, coloring, or any other form of annotation. The annotation can be done using hand gestures or a hand tool, or alternatively, using hands-free gestures and/or voice commands. In certain embodiments special annotation tools, such as a virtual pencil, marker, object insertion tool, measuring tool, or any other tool, can be provided to help the user annotate the AR guidance. The measuring tool can allow clinicians to calculate any dimensions on the AR guidance, such as a distance between points or a diameter of a vessel, or any other measurements. For example, using this tool, clinicians can measure the diameter of a given heart valve or a vessel. Based on the measured diameter, the clinician can choose the size of a given surgical implant and/or insertion catheter.

Figure 6:
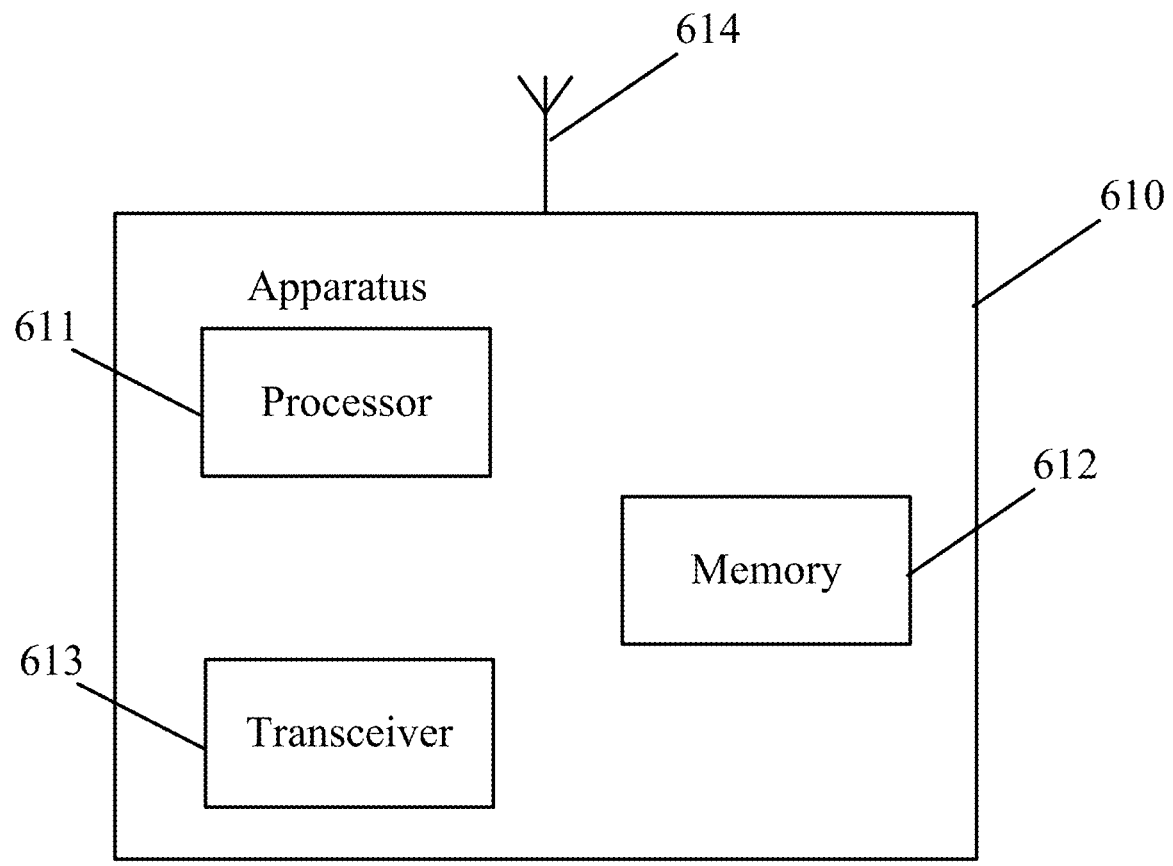
FIG. 6 is a diagram illustrating exemplary components of an AR guidance system according to some embodiments of the disclosed subject matter.

FIG. 6 is an example of an apparatus according to some embodiments of the disclosed subject matter. In particular, FIG. 6 illustrates an apparatus 610 on which the AR guidance is performed, such as an AR head-worn display or an AR guidance apparatus. It should be understood that each feature of FIGS. 1, 2, 3, 4, and 5 and any combination thereof, can be implemented by various apparatus or their combinations, such as hardware, software, firmware, one or more processors and/or circuitry. In one embodiment, the apparatus can include at least one processor, control unit, inertial measurement unit, or module, indicated as 611. At least one memory can be provided in each device, indicated as 612. The memory can include computer program instructions or computer code contained therein. One or more transceiver 613 can be provided, and each device can also include an antenna, illustrated as 614. Although only one antenna each is shown, many antennas and multiple antenna elements can be provided to each of the devices. Other configurations of these devices, for example, can be provided. For example, apparatus 610 can be additionally configured for wired communication, in addition to wireless communication, and in such a case antenna 614 can illustrate any form of communication hardware, without being limited to merely an antenna. The apparatus or device can also include a display coupled to the processor, and used for displaying the augmented reality guidance for the vascular intervention on an optical see-through display, a video see-through display, or any other kind of augmented reality display. In addition, the apparatus or device can include an interface, coupled to the processor, which permits a user to manipulate the displayed augmented reality guidance using zero order rate control or first-order rate control.

Transceiver 613 can each, independently, be a transmitter, a receiver, or both a transmitter and a receiver, or a unit or device that can be configured both for transmission and reception. The transmitter and/or receiver can also be implemented as a remote radio head that is not located in the device itself, but in a mast, for example.

In some embodiments, apparatus 610, such as an AR head-worn display, can include apparatus for carrying out embodiments described above in relation to FIGS. 1, 2, 3, 4, and 5. In certain embodiments, at least one memory including computer program code can be configured to, when executed by the at least one processor, cause the apparatus to perform any or all of the processes described herein.

Processor 611 can be embodied by any computational or data processing device, such as a central processing unit (CPU), digital signal processor (DSP), application specific integrated circuit (ASIC), programmable logic devices (PLDs), field programmable gate arrays (FPGAs), digitally enhanced circuits, or comparable device or a combination thereof. The processors can be implemented as a single controller, or a plurality of controllers or processors.

For firmware or software, the implementation can include modules or a unit of at least one chip set (for example, procedures, functions, and so on). Memory 612 can independently be any suitable storage device, such as a non-transitory computer-readable medium. A hard disk drive (HDD), random access memory (RAM), flash memory, or other suitable memory can be used. The memories can be combined on a single integrated circuit as the processor, or can be separate therefrom. Furthermore, the computer program instructions can be stored in the memory and which can be processed by the processors can be any suitable form of computer program code, for example, a compiled or interpreted computer program written in any suitable programming language. The memory or data storage entity is typically internal but can also be external or a combination thereof, such as in the case when additional memory capacity is obtained from a service provider. The memory can be fixed or removable.

The memory and the computer program instructions can be configured, with the processor, to cause a hardware apparatus such as apparatus 610, to perform any of the processes described above (see, for example, FIGS. 1, 2, 3, 4, and 5). Therefore, in certain embodiments, a non-transitory computer-readable medium can be encoded with computer instructions or one or more computer program (such as added or updated software routine, applet or macro) that, when executed in hardware, can perform a process such as one of the processes described herein. Computer programs can be coded by a programming language, which can be a high-level programming language, such as objective-C, C, C++, C#, Java, etc., or a low-level programming language, such as a machine language, or assembler. Alternatively, certain embodiments can be performed entirely in hardware.

EXAMPLES

The following Examples are offered to illustrate the disclosed subject matter but are not to be construed as limiting the scope thereof.

Example 1

Manipulating 3D Anatomic Models in Augmented Reality

This example illustrates a hands-free approach to augmented reality systems and techniques for performing 3D transformations on patient-specific virtual organ models.

Design

Physician users can rely on visualizing anatomy from specific poses of their choosing. The disclosed interface can support tasks needed during procedures: translating, rotating, and scaling patient-specific virtual anatomic 3D models created for the procedures. Further, the disclosed system can provide physicians with an interaction approach that does not interfere with their workflow. To meet these goals, an AR user interface (UI) initially used manual interaction and was extended to support hands-free interaction.

Head gestures were used as a key component because it suited physician workflow. Foot input can be used for hands-free interaction in the operating room. Certain physicians, however, can use their feet to operate fluoroscopy systems, which play a crucial role in the procedures they perform. Fluoroscopy pedal controls require continuous pressure, which makes simultaneous foot control of other systems impractical.

The disclosed system can reduce the possibility of a user losing sight of virtual content. Certain AR head worn displays (HWDs) have a relatively limited field of view (e.g., approximately 30°×17.5° for HoloLens) in comparison with presently disclosed VR HWD. Relying on head tracking as an input can increase the possibility of losing sight, as the user can move or turn their head away from a selected item in the process of transforming it. To address this, the disclosed system can use interactions based on first-order (i.e., rate) control for transformations that do not involve translation. This can allow physicians to keep virtual models in sight while transforming them (and thus maintain visibility of system status). This also can reduce the need for multiple head gestures to perform a single transformation. The disclosed system can improve standard zero-order manual techniques and reduce user fatigue and frustration.

Implementation

An AR system, which includes the disclosed hands-free UI, written in C# with the Windows 10 Universal SDK, using Visual Studio 2018 (Microsoft, Redmond, Wash.) and the Unity3D engine (Unity Technologies, San Francisco, Calif.) was developed. The application was developed and tested on Microsoft HoloLens. HoloLens supports spatial audio, hand tracking, head tracking, and voice interactions using built-in sensors. However, the disclosed application is device-agnostic, and thus can be run at different screen resolutions on head-worn, hand-held, or desktop devices, whether monoscopic or stereoscopic, with minimal adjustment.

To ensure that the user is constantly aware of the system's status, a cursor can appear in front of the user and follow the forward-facing direction of the user's head. The cursor can provide a set of consistent visual cues for the user as they interact with virtual content. A user can select a virtual model by moving and rotating their head until the cursor is colliding with it. Cursor colors and symbols act as visual cues indicating the currently active interaction technique (hands-free or manual) and the activated transformation (translation, rotation, or scale), respectively.

Hands-Free Interaction

Figure 7:
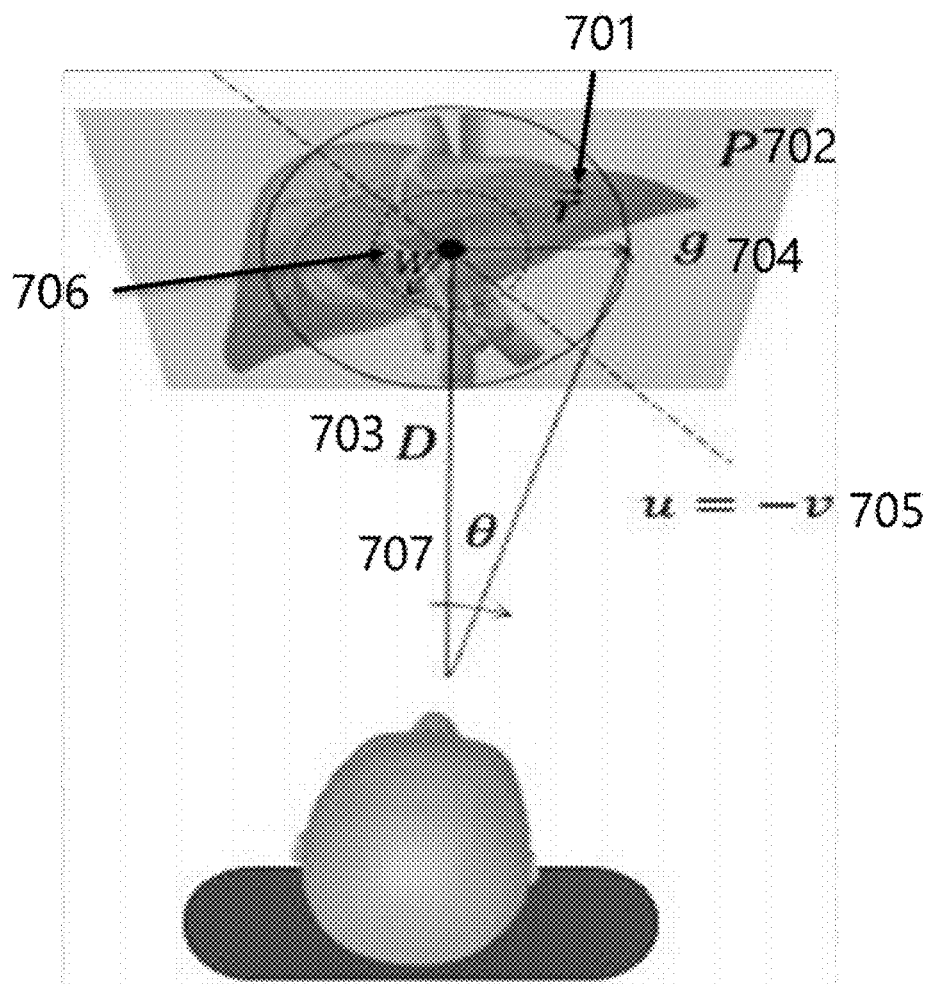
FIG. 7 is a schematic diagram illustrating exemplary hands-free AR techniques according to some embodiments of the disclosed subject matter.

The disclosed system can use voice input to specify the type of interaction technique and type of transformation (e.g., translation, rotation, or scale). The transformation itself can be initiated by voice input and performed by head movement. The disclosed hands-free approach can use head position and orientation to perform all transformations, controlled by the intersection g of the head-gaze direction with a plane P that passes through the model center and faces the user (with the up vector determined by the camera), as shown in FIG. 7. FIG. 7 illustrates that the magnitude of the vector $\vec{r}$ 701, (defined as a vector between center of plane P 702, which passes through the model center and faces user, at distance D 703 from user, and g 704, head-gaze point of a user on plane P 702), can control the rate of transformation. Line u=−v 705, where u and v are horizontal and vertical axes parameterizing plane P 702, is shown, along with the center window of radius W 706.

The hands-free mode can be activated whenever the user says a keyword (e.g., hands-free). A green glow around the cursor icon can be used as a visual cue to indicate that the application is in a hands-free mode. Once in this mode, the user can select a model by hovering g over P of the model and activate the desired transformation mode by saying a voice command. The magnitude and direction of the vector $\vec{r}$ 701 between the model center and g 704 are then used to parameterize the transformation.

Center Window

As long as the cursor remains within a circular center window, the current transformation cannot be applied. When the head rotates such that g lies outside the center window, a transformation can affect the model. The disclosed example system has a center window radius W=6 cm through formative studies with physician users.

The minimum angle θ required to apply a transformation can therefore be calculated as θ=arctan W/D, where D is the distance between the user and the model center (In FIG. 7, θ 707 is larger than this minimum, $|\vec{r}|$>W 706). The larger the distance D, the smaller the angle θ required to initiate a transformation. At the same time, the model can occupy less of the HWD field of view. In this way, a user is able to rotate their head farther without losing sight of the model, thus providing a reliable approach for manipulating distant models. The farther away the head rotates from the center window while a hands-free transformation is active, the greater the effect of the transformation on the model.

Cursor Window

In order to ensure smooth and continuous hands-free transformation, the disclosed system can reduce errors from natural head movement. The position and orientation of the user's head can determine the location of the cursor. If the cursor moves less than a predefined distance (which can be referred to as a cursor window), the transformation persists at its current rate. When the cursor moves outside the cursor window and away from the model center, the transformation can continue at an increased rate. Physician users can seek to pause the transformation without a verbal command, which can take time to recognize. To support this, when the cursor moves outside the cursor window toward the model center, the transformation can be paused. The user can also say "stop" to exit the transformation entirely.

Hands-Free Rotation

Figure 8:
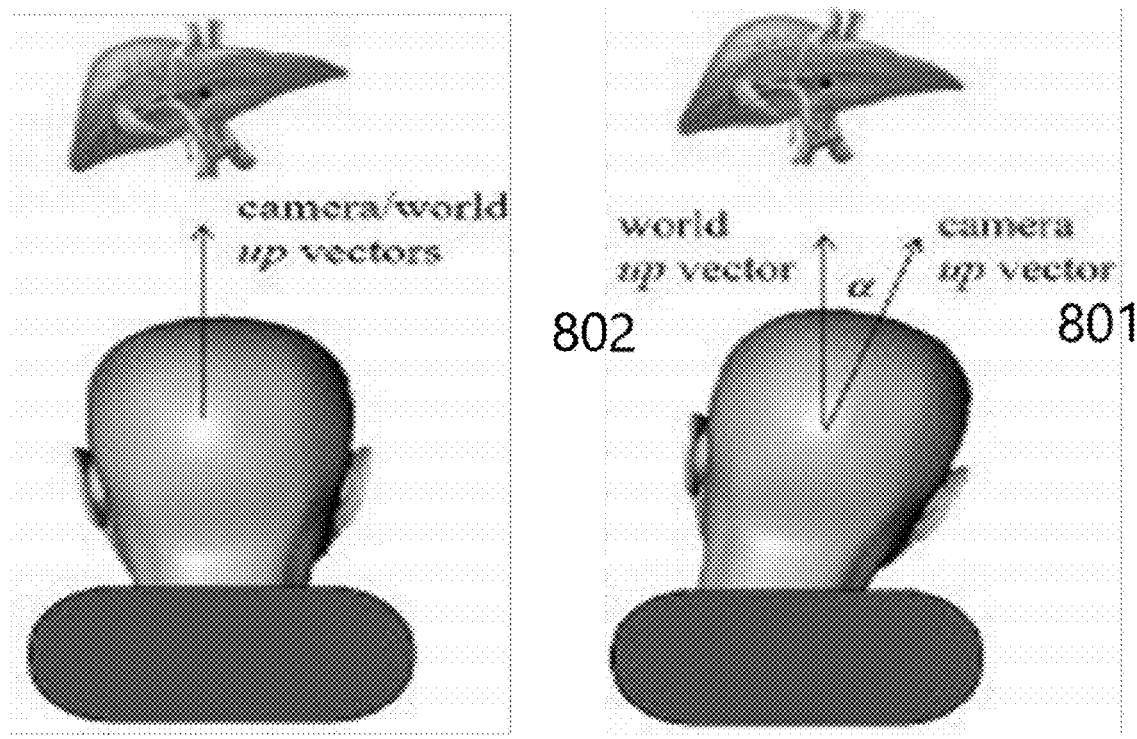
FIG. 8 is a schematic diagram illustrating exemplary hands-free AR techniques using user head roll according to some embodiments of the disclosed subject matter.
Figure 9A:
FIGS. 9A-9B each is a schematic diagram illustrating exemplary hands-free AR techniques based on user head roll according to some embodiments of the disclosed subject matter.
Figure 9B:

This transformation can be activated by saying a keyword (e.g., rotate). The axis about which rotation occurs can be controlled by the angle $\alpha$ between the camera up vector 801 and the world up vector 802 (FIG. 8). While $\alpha < 15°$ (and g is outside the center window), rotation occurs, at speed proportional to $\theta$, about an axis obtained by rotating the vector $\vec{r}$ counterclockwise 90° in plane P (FIG. 7). As shown in FIGS. 9A-9B, when the user rotates their head such that $\alpha \geq 15°$, rotation about axes in plane P is suppressed and hands-free rotation is restricted to be about the axis perpendicular to P from the object center to the user's head, with a speed and direction determined by $\alpha$ (FIG. 8).

Hands-Free Scaling

This transformation can be activated by saying a keyword (e.g., scale or resize). Size is increased (decreased) when g is to the right or above (left or below) the line $u=-v$, shown in FIG. 7, where u and v are horizontal and vertical axes parameterizing plane P. The minimum and maximum sizes can be restricted to half and twice the default size of the model, respectively.

Hands-Free Translation

This transformation can be activated by saying a keyword (e.g., move or translate). The distance D between the user and the model center, along with the offset between the model center and gaze direction as determined by the vector $\vec{r}$, can be stored and used for the duration of the transformation. The model remains at this fixed distance relative to the user and its orientation relative to the user remains constant. Thus, despite its name, this transformation mode can be actually an isometric rigid-body transformation (e.g., not just a translation if the user rotates their head, as in FIG. 8). Hands-free translation can be performed in any direction. For example, translation toward or away from the user can be accomplished by the user either physically moving their head forward or backward (e.g., by walking) or issuing an additional voice command followed by left/down or right/up head rotations to move the selected object backward or forward.

Manual Interaction

This interaction approach was used as a baseline for comparison. The built-in hand tracking support of the Holo-Lens was used, which is equipped with a 120°×120° depth camera, enabling it to detect when a user performs a hand gesture. By default, the HoloLens detects a hand in either the ready state, in which the back of the hand is facing the user, the index finger is raised, and the rest of the fingers are curled, or the pressed state, which differs in that the index finger is down.

Other hand poses were not detected by the HoloLens. Switching from the ready state to the pressed state (performing an air tap) and staying in the pressed state can be referred to as a hold gesture. The manual approach uses the hold gesture to perform all transformations. In this mode, hand gestures and voice commands were used to interact with models.

Manual mode can be activated whenever the user says the keyword (e.g., manual). In addition, this mode can be automatically activated upon the detection of a hold gesture. A blue glow around the cursor icon was used as a visual cue to indicate that the application is in manual mode. Once in manual mode, the user can select a model with the cursor, and activate the desired transformation by speaking a voice command. The user can then perform the hold gesture, moving their hand in any direction The relative translation of the user's hand can be used to parameterize the transformation. For rotation and scaling, this is based on the vector $\vec{v}$, defined as the vector between the start and end positions of the hand maintaining the hold gesture in a single frame, projected onto P. An activated transformation can be applied to the selected model only if the hand moves while in the pressed state. Like the HoloLens's standard manual interaction approach, the disclosed manual interaction approach also uses zero-order control for all transformations.

Manual Rotation

This transformation can be activated by saying a keyword (e.g., rotate). Manual rotation about an axis in plane P is counterclockwise about an axis obtained by rotating $\vec{v}$ counterclockwise by 90° in P. For example, moving the hand left or right rotates the model about a roughly vertical axis in P, while moving the hand up or down rotates the model about a roughly horizontal axis in P. The amount of rotation is linearly related to $|\vec{v}|$, thus accomplishing zero-order control. This transformation can be a variant of the virtual trackball.

Manual rotation about an axis perpendicular to P from the object center to the user's head is performed by saying a keyword (e.g., z-axis). Similar to hands-free scaling, rotation is performed relative to the line $u=-v$ in P, when the user's hand is in the pressed state. The model rotates clockwise when the user's hand moves to the right or up and counterclockwise when the user's hand moves to the left or down.

Manual Scaling

This transformation can be activated by saying a keyword (e.g., scale or resize). The model increases in size when the user's hand moves to the right or up and decreases in size when the user's hand moves to the left or down. As in hands-free scaling, the minimum and maximum sizes can be restricted to half and twice the default size of the model, respectively.

Manual Translation

This transformation is activated by saying a keyword (e.g., move or translate). As the user's hand moves in the pressed state, the position of the model is changed in the direction of the hand movement.

The above embodiments provide significant improvements and advantages to medical procedures by using the described AR technology. Certain embodiments can help make medical procedures, such as vascular interventions faster, safer, and more cost-effective. In particular, the above embodiments help to reduce procedure times, radiation exposure, contrast dose, and complication rates. Further, certain embodiments can eliminate guesswork as to the identity of a given vessel, and help to facilitate access to difficult vessels. By eliminating guesswork, the above embodiments will help to improve procedure outcomes. In addition, as discussed above, some embodiments help a clinician to maintain sterility during a medical procedure, by allowing the clinician to operate or manipulate the AR guidance system without having to physically touch a user interface.

The features, structures, or characteristics of certain embodiments described throughout this specification can be combined in any suitable manner in one or more embodiments. For example, the usage of the phrases "certain embodiments," "some embodiments," "other embodiments," or other similar language, throughout this specification refers to the fact that a particular feature, structure, or characteristic described in connection with the embodiment can be included in at least one embodiment of the disclosed subject matter. Thus, appearance of the phrases "in certain embodiments," "in some embodiments," "in other embodiments," or other similar language, throughout this specification does not necessarily refer to the same group of embodiments, and the described features, structures, or characteristics can be combined in any suitable manner in one or more embodiments.

One having ordinary skill in the art will readily understand that the disclosed subject matter as discussed above can be practiced with procedures in a different order, and/or with hardware elements in configurations which are different than those which are disclosed. Therefore, although the disclosed subject matter has been described based upon these embodiments, it would be apparent to those of skill in the art that certain modifications, variations, and alternative constructions would be apparent, while remaining within the spirit and scope of the disclosed subject matter.

What is claimed is:

1. A method for assisting a clinician in performing a medical procedure on a patient using augmented reality guidance, comprising:
   obtaining a three-dimensional model of an anatomic part of the patient;
   aligning the three-dimensional model with data to form augmented reality guidance for the medical procedure;
   presenting the augmented reality guidance to the clinician during the medical procedure using an augmented reality three-dimensional display;
   manipulating the presented augmented reality guidance using one or more of hands-free gestures, hand gestures, or voice commands; and
   pausing the manipulation of the presented augmented reality guidance by orienting the clinician's head out of a predefined cursor window in a direction back toward a center of the augmented reality guidance.

2. The method of claim 1, wherein the augmented reality three-dimensional display comprises an optical see-through display.

3. The method of claim 1, wherein the manipulation of the augmented reality guidance comprises at least one of rotating, scaling, moving, or changing transparency or coloring of the augmented reality guidance.

4. The method of claim 3, wherein the manipulation of the augmented reality guidance comprises using a head gesture to perform at least one of first-order control or zero-order control, wherein the first-order control comprises at least one of the rotating or scaling of the augmented reality guidance, and wherein the zero-order control comprises the moving of the augmented reality guidance.

5. The method of claim 1, wherein the data comprises live imaging data.

6. The method of claim 5, wherein the aligning of the three-dimensional model of the patient's anatomy with the data to form the augmented reality guidance comprises fusing the three-dimensional model and the live imaging data or using the live imaging data to localize a position within the three-dimensional model.

7. The method of claim 5, wherein the live imaging data comprises live two-dimensional fluoroscopy.

8. The method of claim 5, wherein the live data is presented in alignment with the three-dimensional model by the augmented reality three-dimensional (3D) display.

9. The method of claim 5, wherein the live data is presented on an external display, and the three-dimensional model is presented by the augmented reality three-dimensional (3D) display in alignment with the live data.

10. The method of claim 1, wherein the method of aligning comprises at least one of machine learning, optical character recognition, input from an inertial measurement unit, physical trackers, or image recognition.

11. The method of claim 1, further comprising:
    selecting at least one manipulation mode of the augmented reality guidance using a voice command.

12. The method of claim 1, wherein the three-dimensional model of the anatomy of the patient is obtained using computed tomography, magnetic resonance imaging, or other forms of volumetric imaging.

13. The method of claim 1, further comprising adjusting the three-dimensional model to align with the live data.

14. The method of claim 1, further comprising tracking a C-arm orientation and position to align the three-dimensional (3D) model with the live data.

15. The method of claim 1, further comprising presenting the augmented reality guidance to a plurality of users concurrently.

16. The method of claim 1, further comprising adjusting a size of the three-dimensional model to correspond to a size of a patient's body.

17. The method of claim 1, wherein the augmented reality guidance further comprises at least one of previously-acquired patient data, real-time patient data, or medical documents.

18. The method of claim 1, further comprising recording data associated with the augmented reality guidance for the medical procedure; and storing the recorded data in a database.

19. An apparatus for assisting a clinician in performing a medical procedure on a patient using augmented reality guidance, comprising:
    an augmented reality three-dimensional display;
    at least one memory comprising computer program code; and
    at least one processor;
    wherein the computer program code is configured, when executed by the at least one processor, to cause the apparatus to:

obtain a three-dimensional model of an anatomic part of a patient;
align the three-dimensional model with data to form the augmented reality guidance for the medical procedure;
present the augmented reality guidance for the medical procedure using the augmented reality three-dimensional display;
manipulate the presented augmented reality guidance using one or more of hands-free gestures, hand gestures, or voice commands; and
pausing the manipulation of the projected augmented reality guidance by orienting the clinician's head out of a predefined cursor window in a direction back toward a center of the augmented reality guidance.

20. A non-transitory computer-readable medium encoding instructions that, when executed in hardware, perform a process comprising:
obtaining a three-dimensional model of an anatomic part of the patient;
aligning the three-dimensional model with data to form augmented reality guidance for the medical procedure;
presenting the augmented reality guidance to a clinician during the medical procedure using an augmented reality three-dimensional display;
manipulating the presented augmented reality guidance using one or more of hands-free gestures, hand gestures, or voice commands; and
pausing the manipulation of the projected augmented reality guidance by orienting the clinician's head out of a predefined cursor window in a direction back toward a center of the augmented reality guidance.

21. The non-transitory computer-readable medium of claim 20, wherein the manipulation of the presented augmented reality guidance comprises at least one of rotating, scaling, moving, or changing transparency or coloring of the presented augmented reality guidance.

* * * * *

UNITED STATES PATENT AND TRADEMARK OFFICE
CERTIFICATE OF CORRECTION

| | | |
|---|---|---|
| PATENT NO. | : 11,666,385 B2 | Page 1 of 1 |
| APPLICATION NO. | : 16/796645 | |
| DATED | : June 6, 2023 | |
| INVENTOR(S) | : Steven Feiner et al. | |

It is certified that error appears in the above-identified patent and that said Letters Patent is hereby corrected as shown below:

In the Specification

In Column 1, Lines 24-27, under the heading, STATEMENT REGARDING FEDERALLY SPONSORED RESEARCH:
"This invention was made with government support HL07616 awarded by the National Institutes of Health and 1514429 awarded by the National Science Foundation. The government has certain rights in the invention."
Should read:
-- This invention was made with government support under HL007616 awarded by the National Institutes of Health, and 1514429 awarded by the National Science Foundation. The government has certain rights in the invention. --

Signed and Sealed this
Fourth Day of June, 2024

Katherine Kelly Vidal
*Director of the United States Patent and Trademark Office*